United States Patent [19]
Howes

[11] 4,129,824
[45] Dec. 12, 1978

[54] ELECTRONIC HYDROMETER

[76] Inventor: Edward P. Howes, 1244 Montgomery St., Salt Lake City, Utah 84104

[21] Appl. No.: 743,861

[22] Filed: Nov. 22, 1976

[51] Int. Cl.$^2$ ............................................. G01N 27/42
[52] U.S. Cl. ................................. 324/29.5; 324/30 B; 324/61 R
[58] Field of Search ............ 73/32 R; 324/61 R, 30 B, 324/29.5, 29, 30 R; 320/48

[56] References Cited

U.S. PATENT DOCUMENTS

| | | | |
|---|---|---|---|
| 3,283,240 | 11/1966 | Spady | 324/30 B |
| 3,376,746 | 4/1968 | Roberts | 324/61 R |

OTHER PUBLICATIONS

E. Willihnganz, Battery Impedance, Electrical Engineering, Sep. 1959, vol. 78, No. 9, pp. 922–925.

Primary Examiner—M. Tokar
Attorney, Agent, or Firm—Mallinckrodt & Mallinckrodt

[57] ABSTRACT

An electronic hydrometer for monitoring the specific gravity of a solution containing ions includes a probe having spaced apart electrodes adapted to be inserted into the solution to be monitored and is provided with an A.C. resistance electrically connected in series with an electrode of the probe to form, with the probe, a voltage divider network. Means for applying an A.C. voltage across the network and means for generating a reference voltage are provided. The voltage across one element of the voltage divider network is compared with the reference voltage, the difference in voltages being an indication of solution specific gravity. Suitable means, such as a meter, is provided for comparing the voltages and indicating the voltage difference.

23 Claims, 5 Drawing Figures

ELECTRONIC HYDROMETER

BACKGROUND OF THE INVENTION

1. Field

This invention is in the field of devices for monitoring specific gravity of a solution, and is particularly concerned with monitoring continuously electronically.

2. State of the Art

Float type hydrometers have been used for many years to measure the specific gravity of a solution. These, however, do not lend themselves to continuous, remote monitoring of the solution. It is known that solutions containing ions will support a current flow and that the resistance to current flow between two electrodes immersed in such a solution is a function of the specific gravity of the solution. Thus, by measuring the resistance of the solution, an indication of the specific gravity of the solution can be obtained. Various circuits utilizing conductivity probes have been suggested. However, those that utilize a D.C. voltage across the electrodes in the probe generate considerable gas at the surface of one or both of the probes, which interferes with accuracy of measurement. Further, such probes have generally been directly connected to a meter that indicates current flow through the solution being measured. Since the current changes that take place with changes in specific gravity are usually very small and difficult to detect directly with a meter, accuracy is lacking in such systems. Systems applying A.C. voltage across a conductivity cell have been suggested, but have used complicated arrangements for the substitution of series and shunt resistances so that voltage across the conductivity cell varies in accordance with the logarithm of the conductivity measured by the cell. These prior systems all leave much to be desired.

3. Objective

It was a principal objective of the invention to provide a simple and easy to use and maintain electronic system for measuring variations in specific gravity of a solution.

SUMMARY OF THE INVENTION

According to the invention, a probe having spaced apart electrodes is adpated to be inserted into and remain in the solution being monitored. An A.C. resistance is electrically connected in series with an electrode of the probe to form, with the probe, a voltage divider network having the probe and A.C. resistance as elements thereof. An A.C. voltage is applied across the network causing an A.C. voltage to appear across the probe and across the resistance.

Since the resistance of the solution varies with changes in specific gravity, the voltage across the probe will vary with changes in specific gravity. Voltage across the A.C. resistance will vary inversely to the voltage variation across the probe. Thus, the voltage across either element of the divider network may be used as a measure of the specific gravity of the solution.

The change in voltage over a useful range of specific gravities is generally small in comparison to the absolute voltage measured. Therefore, in order to be able to more accurately read the change in voltage which occurs, it is necessary to begin measuring at a voltage level within the range of voltages of interest, preferably at a voltage representing an extreme of the possible range to be measured. This may conveniently be a voltage representative of the lowest possible specific gravity to be measured. To accomplish this, means for generating a reference voltage is provided. Means are electrically connected to compare the voltage across one element of the divider network to the reference voltage, the difference in voltage providing a measure of specific gravity.

Since the resistance of the solution, and thus the voltage appearing across the probe, will be a function of the temperature of the solution as well as of its specific gravity, it is preferred that a temperature sensor be included in the probe to sense the temperature of the solution to be monitored. The temperature sensor is electrically a part of the means for generating a reference voltage so that the reference voltage produced varies with the temperature of the solution being monitored. In this way, the results of the voltage comparison is corrected for any changes in solution temperature and the resulting voltage difference will be caused solely by the solution specific gravity.

The present invention is particularly adapted for measuring the specific gravity of an acid solution in an acid-lead storage battery. The specific gravity of the solution in the battery is an excellent indicator of the amount of charge remaining in the storage battery. Thus, by monitoring the specific gravity, the amount of charge is also monitored. This is particularly useful in vehicles or other equipment that are powered by electricity from storage batteries. For example, with an electric car it is necessary to known when to stop and recharge the battery. This is not only to prevent running out of power, but also to avoid permanent damage to the batteries which can result from being totally discharged.

DRAWINGS

The best modes presently contemplated of carrying out the invention are illustrated in the attached drawings in which:

FIG. 1 is a block diagram representing the generic invention;

FIG. 2, a more specific block diagram which includes provision for temperature compensation.

FIG. 3, a circuit diagram of a presently preferred embodiment adapted to be powered from a D.C. voltage source;

FIG. 4, a side elevation of a probe suitable for use in the invention; and

FIG. 5, a bottom plan of the probe.

DETAILED DESCRIPTION OF THE ILLUSTRATED EMBODIMENTS

Figure 1:
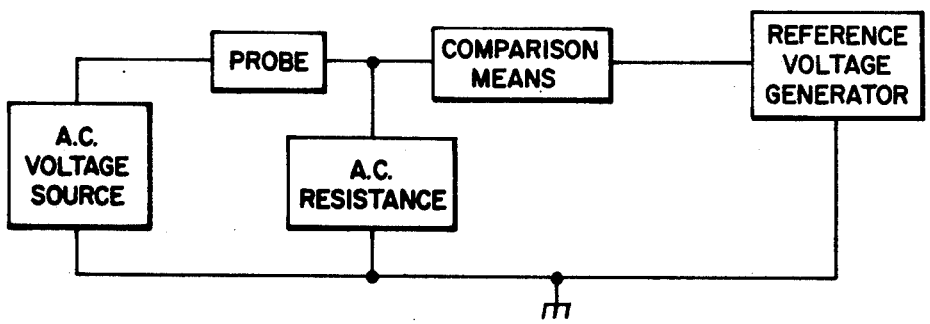
Figure 2:
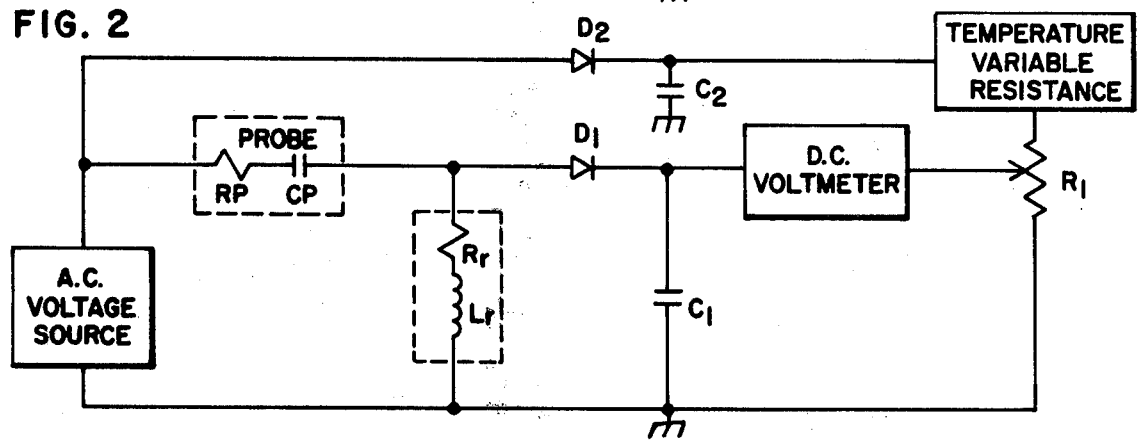

An electronic hydrometer, which, in accordance with the invention, can continuously monitor the specific gravity of a solution containing ions, is shown in its essentials by the block diagram of FIG. 1. The probe comprises spaced apart electrodes and is adapted to be immersed in the solution to be monitored. It acts electrically as a resistance and capacitance, as indicated in FIG. 2 at Rp and Cp. An A.C. resistance is connected electrically in series with the probe to form, with the probe, a voltage divider network. The resistance may be a pure resistor or may be a coil, in the latter case there will be a resistance component and an inductance component as indicated at Rr and Lr, respectively, in FIG. 2. A source of A.C. voltage is connected across the probe and A.C. resistance forming a closed A.C. circuit for current flow. The applied voltage is divided so a portion of it appears across a probe and a portion across the resistance. As the resistance of the probe changes the voltages across the probe and resistance change inversely. Thus, as the specific gravity of a solution increases, its resistance to current flow decreases and the voltage across the probe will decrease. The voltage across the resistance will accordingly increase. The reverse is true if the specific gravity of the solution decreases. The voltage across either element of the divider, i.e. the probe or the resistance, may be used as a measure of specific gravity of the solution.

A.C. current flow through the probe is advantageous because it significantly reduces and in most cases eliminates completely the problem of gas generation at the faces of contact between the probe electrodes and the solution being monitored. As previously noted, gas generation is a problem when D.C. voltage and current are used.

The change in voltage appearing across the elements of the divider corresponding to a change in specific gravity, will generally be relatively small in comparison to the absolute value of the voltages. For example, the change in voltage over the possible range of specific gravity to be measured may be 0.2 volts, with the actual voltage varying between 6 volts and 6.2 volts. Thus, an indicator which measures the absolute voltage would show only a very small change and the specific gravity would be difficult to read. For this reason, a reference voltage is generated and the measured voltage is compared to the reference, as shown in FIG. 1, where the voltage across the A.C. resistance is shown as the measured voltage. It is preferred to generate a reference voltage which equals the measured voltage at one of the extremes of the possible range of specific gravity to be measured. For example, the reference voltage may be conveniently set to equal the minimum voltage generated across the divider element measured over the desired range of possible specific gravities.

If the voltage across the element measured varies from 6 volts to 6.2 volts over the desired range of possible specific gravities, the reference voltage would be set at 6 volts. If the solution is at the lowest point of its desired possible range, a comparison of the measured voltage with the reference voltage will indicate zero difference. If the solution is at the highest specific gravity in the possible range, a comparison of the voltages will indicate a maximum difference in voltage, or, for the above example, 0.2 volts. If a voltmeter is used to read the difference in voltage, the range of the meter could be chosen to be 0.2 volts thus producing a full scale deflection indicating maximum specific gravity with a full range of measurement down to the minimum possible value of interest.

The resistance of a solution will vary with temperature as well as specific gravity. The voltage changes across the element of the divider measured due to temperature changes could be of the same order of magnitude as those due to changes in specific gravity. It is therefore desireable to provide some form of temperature compensation unless the solution monitored can easily be maintained at a substantially constant temperature. For compensation purposes, a sensor may be arranged in conjunction with the means for generating the reference voltage so that the reference voltage varies with the temperature of the solution being monitored in similar fashion as the measured voltage. For example, if the reference voltage is set to correspond to the lowest measured voltage of a possible range, the reference voltage would change with temperature change of the solution so that it would correspond to the lowest measured voltage at all possible temperatures of interest.

FIG. 2 shows a more detailed block diagram similar to FIG. 1, but including means for temperature compensation. An A.C. voltage is supplied by the A.C. voltage source. The probe is indicated as having a resistance component Rp and a capacitance component Cp and the A.C. resistance is shown as having a resistance component Rr and an inductance component Lr. To facilitate comparison of the measured voltage with the reference voltage, the reference voltage is generated as a D.C. voltage and the measured voltage is converted to a D.C. voltage for comparison. Comparison of A.C. voltages is more difficult because of the phase shift in the A.C. that occurs across the voltage divider network due to changes in the capacitance component of the probe with changes in solution temperature. In order to convert the measured voltage to a D.C. voltage a diode D1 and capacitor C1 are arranged in series and the series arrangement is connected in parallel with the A.C. resistance. Thus arranged, the diode passes the positive cycle of the A.C. voltage appearing across the resistance and a positive, proportional, D.C. voltage appears across the capacitor. A second diode D2 and capacitor C2 arranged in series provides a D.C. voltage across capacitor C2. The voltage across C2 is applied to a voltage divider network made up of a fixed resistance R1 and a temperature variable resistance connected in series. At least a portion of the temperature variable resistance is preferably located in the probe, or at least within the solution being monitored. The resistance of the temperature variable resistance changes with changes in solution temperature. As the resistance vaires, the voltage drop across it will vary and the voltage drop across the resistance R1 will vary inversely. The resistance of resistor R1 and the resistance range of the temperature variable resistance are chosen so that the voltage variations with temperature across the fixed resistance are equal to the voltage variations that occur across capacitor C1. The actual voltage comparison can be made by a D.C. voltmeter connected between the capacitance C1 and the variable portion of the resistance R1. The variable resistance is used for calibration of the reference voltage. The actual reference voltage for comparison purposes being the voltage of the wiper of resistance R1.

The present invention has particular application in the field of monitoring lead acid storage batteries that are used to power electrical equipment and electrical vehicles. As the batteries discharge, they reach a point where they must be recharged before further use of the equipment they are powering. If a storage battery becomes completely discharged, apart from the inconvenience of running out of power, permanent damage may be done to the battery. It is, therefore, important to know when the battery must be recharged.

In the standard lead acid storage battery the specific gravity of the acid solution is an excellent indicator of the charge remaining in the battery. To the degree of accuracy required for monitoring charge remaining in the battery, the relationship between specific gravity and charge may be assumed to be linear. The specific gravity of the acid solution will vary between about 1.150 and 1.300 for discharged and charged conditions respectively.

Figure 3:
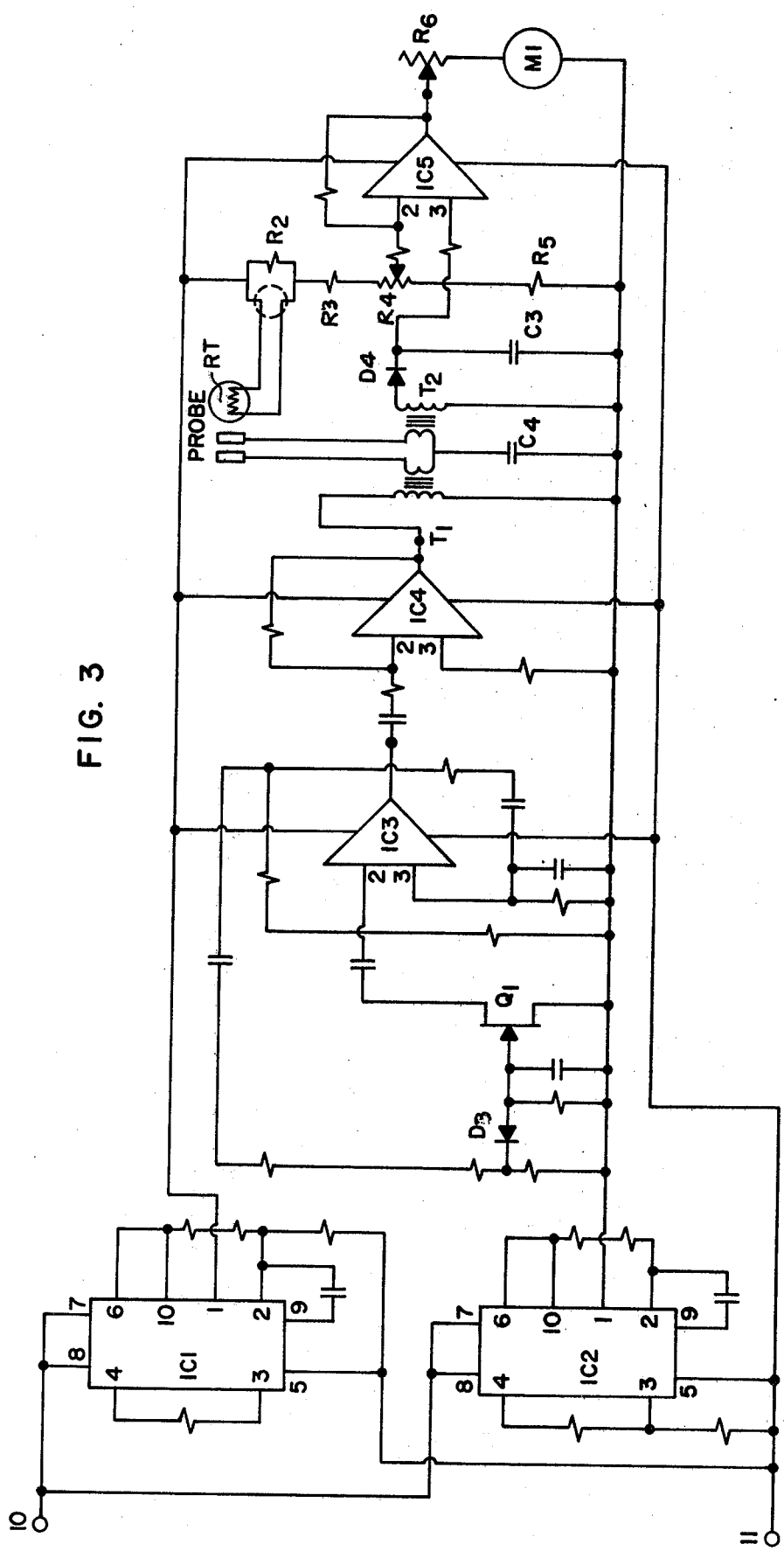

FIG. 3 shows circuitry specifically adapted for monitoring the specific gravity of a lead acid storage battery. The circuit is designed to be powered by the battery being monitored, although it could be powered from a separate power source. Circuit terminals 10 and 11 are connected to the battery so that terminal 10 is positive and terminal 11 is negative.

Since the circuitry itself requires both positive and negative voltage with respect to ground, two voltage regulators are included. One regulator gives a regulated output of half the other regulated output and such half output is used as ground potential for the circuitry. In this way equal plus and minus voltages are available to power the circuit components.

As illustrated in FIG. 3, IC 1 and IC 2 are both integrated circuit voltage regulators. While any type of regulator that gives desired voltage values may be used, a type 723 regulator has been found satisfactory. The numbers shown adjacent inputs and outputs to the various integrated circuits are the terminal numbers for those circuit inputs and outputs.

IC 1 is connected in the standard fashion as indicated on the manufactures specifications sheet and the external resistors are chosen to give a regulated output voltage of 6.4 volts. The connections shown are as indicated in FIG. 2 of Radio Shack Data Sheet for the RS-723 Precision Voltage Regulator.

IC 2 is connected in standard fashion with external resistances chosen to give a regulated output voltage one-half the voltage of IC 1 or 3.2 volts. The connections shown are as illustrated in FIG. 1 of the same Radio Shack Data Sheet.

The actual values of the voltage outputs of IC 1 and IC 2 are not critical as long as the output of IC 2 is one-half that of IC 1. The value of IC 1 however, should be chosen to be far enough below the lowest expected value of the input voltage so that good regulation of the output occurs over any expected variations of input voltage. The 6.4 volt value for IC 1 has been found satisfactory for use with inputs from a standard 12 volt storage battery which may vary in voltage over a range from about 8 volts to about 13.5 volts between a discharged and charged condition. Since similar regulators are used and each have similar temperature variations, the ratio of the two voltages will remain constant even though the actual values may change slightly with changes in ambient temperature.

The 3.2 volt output from IC 2 is used as the ground level for the remainder of the circuit. The 6.4 volt output from IC 1 becomes a positive 3.2 volts with respect to the output of IC 2 and the negative battery terminal 11 become a negative 3.2 volts with respect to the output of IC 2.

The outputs of the voltage regulators are connected to an oscillator which includes diode D3, field effect transistor Q1, and operational amplifier IC 3. The circuitry shown for the oscillator is standard and is shown on Calectro data sheet No. 1R 8118 dealing with operational amplifiers. The circuitry produces a sine wave output from IC 3 with a frequency of about 3 KHz (the data sheet indicates an output of 1 KHz), however, the frequency is not critical.

The output from the oscillator is connected to IC 4, an operational amplifier connected in standard fashion as a buffer amplifier. IC 4 amplifies the sine wave signal from IC 3 and isolates it from the remaining circuitry so that output loading of the oscillator causing distortion of the sine wave does not occur.

The signal from IC 4 is the A.C. voltage signal to be applied to the probe. Direct connection to the probe, however, is not recommended where the battery being monitored is the one supplying the power to the monitoring circuit.

The normal storage battery is made up of a series of separate cells, each cell producing a part of the voltage for the battery. In the usual lead-acid 12 volt storage battery, the potential in each cell starting at one terminal, increases by 2 volts until the other terminal is reached. It is therefore preferred to isolate the probe so that any D.C. voltage level is a particular cell will have no effect on the remainder of the circuitry.

The probe is shown as transformer coupled to the A.C. voltage source. The sine wave output of IC 4 is connected to the primary of transformer T1. The secondary of T1 is connected to one electrode of the probe and to the primary winding of transformer T2 which is also connected to the second electrode of the probe.

With an A.C. voltage across the primary of T1, and A.C. voltage appears across the secondary of T1, across the probe electrodes, and across the primary of transformer T2. An A.C. current loop is set up through the probe, secondary of T1, and primary of T2. A current will flow in the primary of T2 whether or not secondary current flows in T2.

The circuitry of FIG. 3 discussed so far, up to the secondary of T1, comprises the A.C. voltage source of FIGS. 1 and 2. The A.C. voltage is applied to the probe and to the primary of T2. The primary of T2 comprises the A.C. resistance of FIGS. 1 and 2.

The transformers T1 and T2 may be of various types. As shown, transformer T1 is a step down transformer reducing the voltage output of IC 4 from somewhere in the range of 2 to 3 volts peak-to-peak to somewhere in the range of 1 to 2 volts peak-to-peak. Transformer T2 is shown as a step up transformer, increasing the voltage across the primary of T2 from somewhere in the range of 0.2 to 0.3 volts to 0.8 to 1 volts. The transformers could be merely isolation transformers with a 1 to 1 ratio, or could be other combinations of step up and step down transformers. Alternately, the probe could be isolated by use of capacitors rather than transformers.

A diode D4 and capacitor C3 (corresponding to diode D1 and capacitor C1, respectively, in FIG. 2) are connected in series with the secondary of transformer T2. During the positive half-cycle of A.C. voltage produced by the secondary of T2, current is passed by diode D4 and a D.C. voltage is built up on capacitor C3. The voltage on capacitor C3 is proportional to the specific gravity of the solution being monitored, as has been explained. For the various voltage values given above as being typical for the present circuit, a voltage of approximately 0.4 volts will be built up on C3 and the voltage change on C3 to be measured over the changes in specific gravity of interest will be only about 2 millivolts.

In order to compensate for the changes in the resistance of the solution with changes in solution temperature, it is preferable that a temperature sensitive resistance be located in contact with the solution being monitored. A common glass bead type thermistor, such as a Fenwell 6B 40P, located in the probe as at 12, FIGS. 4 and 5, has been found to be satisfactory for this purpose.

The thermistor, indicated at Rt in FIG. 3, is electrically placed in parallel with a fixed resistor R2, which, in series with resistors R3, R4, and R5, form a voltage divider network. The divided voltage appears on the wiper comprising the variable portion of resistor R4. The divider is connected between the output of IC 1, the positive supply to the circuitry, and the output of IC 2, the circuitry ground. This voltage divider network is the reference voltage generator of FIG. 1.

The thermistor referred to above has a nominal resistance value of 40,000 ohms at 0° C. and 5500 ohms at 50° C. plus or minus 20%. The value of resistor R2 is parallel with the thermistor Rt is chosen so that the parallel combination will produce a resistance change in the voltage divider, with solution temperature change, that causes a voltage change at the wiper of resistor R4 equal to the voltage change which occurs across capacitor C3 due to the same temperature change. For example, if a solution of constant specific gravity produces a voltage on capacitor C3 of 0.400 volts at 0° C., the voltage divider would be adjusted to provide a voltage of 0.400 volts at the wiper of R4. If the same solution at 50° C. produces a voltage of 0.401 volts on a capacitor C3, the parallel combination of Rt and R2 is adjusted so that for that same temperature change of the solution, the resistance change is such that a voltage of 0.401 volts appears at the wiper of R4.

The resistances needed in any particular case may be found using the well known equation for voltage produced by a voltage divider, $V_{out}$ (voltage at wiper of R4 in FIG. 3), having a resistance A (total combined resistance of Rt, R2, R3, and the portion of R4 above the wiper in FIG. 3) and a resistance B (total combined resistance of the portion of R4 below the wiper and R5 in FIG. 3):

$$V_{out} = V_{in} \frac{A}{A + B},$$

where $V_{in}$ in the voltage applied to the divider. By knowing $V_{in}$ and a desirable $V_{out}$ and by picking a desirable total resistance A+B to produce a suitable current in the divider circuit (current level is arbitrary), the relative values of A and B may be found. Then, by knowing the desired change in $V_{out}$ and knowing that B will remain constant and that the change in $V_{out}$ will be determined by the change in the resistance of A, the same equation may be used to determine the required resistance change of A.

Knowing that the resistance R of the parallel combination of resistors Rt and R2 is:

$$R = \frac{Rt \times R2}{Rt + R2},$$

and knowing the change in Rt (the thermistor) over a certain temperature range, the resistance of R2 can be found by subtracting the expression for R at one known value of Rt from the expression for R at the other known value of Rt and setting that difference equal to the desired resistance difference of A as calculated. Of course, if a temperature variable resistance can be found which has the desired resistance change over the desired temperature range, the parallel combination of Rt and R2 would be unnecessary.

Once the proper resistance change is achieved, the series resistances R3 and the portion of R4 above the wiper, are chosen to give the proper total resistance of A for the voltage divider.

Since the voltage change on capacitor C3 and thus the voltage difference to be measured in the illustrated circuitry is only about 2 millivolts, it is desirable to amplify the voltage difference before reading this difference with a meter. Therefore, the voltage on capacitor C3 is fed to one input of IC 5. The voltage on the wiper of resistor R4 is fed to a second input of IC 5. IC 5 is an integrated circuit operational amplifier which is connected to amplify the difference between its two inputs. The output of IC 5, the amplified difference in voltage level of input signals, is connected through variable resistor R6 to DC voltmeter M1. R6 is used to adjust the full scale reading of the meter to coincide with the highest solution specific gravity of interest. The range of the meter will be selected to be compatible with the range of outputs of IC 5. With the voltage change across C3 of 2 millivolts, and an amplification factor of 1000 for amplifier IC 5, the voltage range of M1 should be between 0 and 2 volts.

In this manner, the meter will read full scale for the highest specific gravity of interest, zero for the lowest, and proportionally for the points between. The meter may be calibrated directly in units of specific gravity, or may be calibrated with a safe operating section, a charge section, and a danger section, or merely as full and empty with gradations in between.

Rather than a meter, the readout could be digital or could merely be a warning light that goes on when the voltage difference becomes less than a preset value.

While several types of operational amplifiers are available and may be used for IC 3, IC 4, and IC 5, a type 741 has been found satisfactory.

While the output of the present circuitry has been found to be stable enough over the normal range of ambient temperatures in which it is most likely to be used so that the measurements of specific gravity are unaffected by ambient temperature changes, in some cases of extreme temperature ranges, or with other circuitry which may be more affected by the ambient temperature changes, provision for additional temperature compensation could be made. Such additional temperature compensation could be accomplished by the provision of a second thermistor located within the circuitry to sense ambient temperatures and electrically connected in parallel or in series with the thermistor monitoring the solution temperature. In this way the thermistor is part of the temperature variable resistance. The temperature variable resistance as a whole is adjusted to compensate for the combined effects of solution temperature and ambient temperatures in the same manner as explained for compensation for changes in solution temperature only.

In monitoring a usual storage battery, the assumption is made that all cells will read substantially the same voltage and therefore that a single probe in one cell will give a valid indication as to the charge left in the entire battery. This assumption is valid for a storage battery in good condition. Conventional tests may be used to determine if a battery is no longer in good condition.

Figure 4:
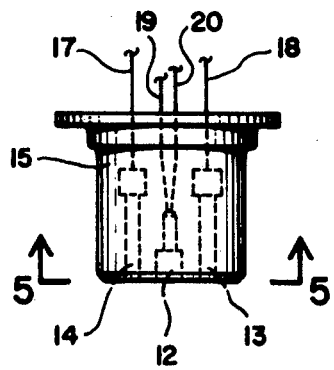
Figure 5:
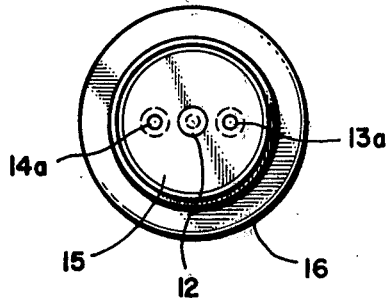

Various types of probes having two spaced-apart electrodes are satisfactory for use with the circuitry of the present invention. An example of a probe which has been found satisfactory for use in the acid solution of a standard lead acid storage battery is shown in FIGS. 4 and 5. Two graphite rods 13 and 14 form the electrodes and are positioned in spaced-apart relationship with the thermistor 12 positioned therebetween. The entire assembly is potted in a plastic potting material 15 so that the electrodes are protected by the potting material from the acid solution. Only the ends of the electrodes 13a and 14a are exposed directly to the solution. This probe may be attached to the bottom of the usual battery cell cap indicated as 16, so that it will be positioned in the battery acid when the cap is in position in the battery. Leads 17, 18, 19, and 20 connect the two electrodes 13 and 14 and the thermistor 12 respectively, to the remainder of the circuitry which will usually be placed at a location remote from the battery itself. Carbon rods of 0.047 inch diameter spaced 0.30 inch apart center to center, or pencil leads of 0.5 millimeter diameter spaced the same distance apart, have been found satisfactory for such a probe.

A capacitor C4, FIG. 3, is connected as shown to reduce high frequency noise that may be picked up in the conductors leading from the probe to the remainder of the circuitry. High frequency noise becomes a problem particularly when the system is installed in an automobile and the probe conductors run through the engine compartment. Capacitor C4 eliminates this problem.

Whereas the invention is specifically illustrated and described with respect to presently preferred embodiments thereof, and specifics of the invention intended for a particular use are given, it should be understood that other embodiments can be constructed from the teachings hereof without departing from the inventive concepts defined by the claims.

I claim:

1. An electronic hydrometer for continuously monitoring during use of a lead acid battery the amount of charge remaining in the battery by monitoring the specific gravity of the acid solution in the battery, comprising a probe for insertion into the battery solution to be monitored, said probe having electrodes in spaced apart relationship; an A.C. resistance electrically connected in series with an electrode of the probe to form, with the probe, a voltage divider network having said resistance and said probe as elements thereof; means for converting D.C. voltage from the battery being monitored to A.C. voltage and supplying such A.C. voltage across said network, said means being capable of supplying full A.C. voltage across said network even when the battery is in a close to fully discharged condition so that they hydrometer will remain fully powered over a wide range of battery conditions; means for generating a reference voltage; and means for comparing the A.C. voltage across one of the elements of the voltage divider network with the reference voltage, whereby voltage difference is indicated and is calibrated in terms of the amount of charge remaining in the battery being monitored.

2. An electronic hydrometer according to claim 1 wherein the means for converting D.C. voltage from the battery to A.C. voltage includes an oscillator adapted to operate on a D.C. voltage less than the voltage of the battery when in a close to fully discharged condition and connected to supply an A.C. voltage across the voltage divider network, and a voltage regulator electrically connected between the battery and the oscillator and adapted to supply a regulated voltage to the oscillator, said voltage having a value less than that of the battery when in a close to fully discharged condition.

3. An electronic hydrometer according to claim 2 wherein the probe comprises two spaced apart electrodes having all but one of their ends embedded in a plastic material, the said one end of each electrode being exposed on the acid solution being monitored.

4. An electronic hydrometer according to claim 3, wherein the probe is secured to and carried by one of the normal battery cell caps of the battery.

5. An electronic hydrometer according to claim 1, wherein the means for generating a reference voltage is arranged to produce a voltage that is substantially equal to the voltage across that element of the voltage divider being measured which corresponds to one extreme of the possible range of specific gravities to be monitored.

6. An electronic hydrometer according to claim 1, wherein the means for generating a reference voltage is adapted to produce a D.C. voltage; and wherein the comparing means includes means for converting the A.C. voltage across that element of the voltage divider being measured to a D.C. voltage before comparison thereof with the reference voltage.

7. An electronic hydrometer according to claim 9, wherein that element of the divider being measured is the A.C. resistance; and wherein the means for converting the A.C. voltage across said A.C. resistance to a D.C. voltage comprises a series arrangement of a rectifier and capacitor electrically connected in parallel with the A.C. resistance, the D.C. voltage across the capacitor being the voltage that is compared with the reference voltage.

8. An electronic hydrometer according to claim 7, wherein the comparing means includes a voltmeter electrically connected between the capacitor and the reference voltage, so that the meter indicates the difference in voltage between the two.

9. An electronic hydrometer according to claim 7, wherein the comparing means includes an amplifier which generates an output signal representative of the difference in voltage between the reference voltage and the voltage across the capacitor, and a meter to indicate the output of the amplifier.

10. An electronic hydrometer according to claim 1, wherein a temperature sensor is located in the probe to sense the temperature of the solution being monitored, said temperature sensor being electrically a portion of the means for generating a reference voltage, so that the reference voltage is a function of the temperature of the solution being monitored.

11. An electronic hydrometer according to claim 10, wherein the temperature sensor is a temperature-controlled, variable resistance.

12. An electronic hydrometer according to claim 11, wherein the means for generating a reference voltage includes a D.C. voltage source and a voltage divider network with two portions, one portion being a fixed resistance, the other portion being the temperature variable resistance, the reference voltage being the voltage across one portion of the network.

13. An electronic hydrometer according to claim 12, wherein the temperature variable resistance portion of the network includes both fixed and temperature variable resistances.

14. An electronic hydrometer according to claim 13, wherein the A.C. voltage across the A.C. resistance is the voltage that is compared to the reference voltage, and wherein the comparing means includes a series arrangement of a rectifier and capacitor in parallel with the A.C. resistance to convert the A.C. voltage across the A.C. resistance to a D.C. voltage across the capacitor, the D.C. voltage across the capacitor being the voltage that is compared with the reference voltage.

15. An electronic hydrometer according to claim 14, wherein the comparing means includes a voltmeter electrically connected between the capacitor and the reference voltage, so that the meter indicates the difference in voltage between the two.

16. An electronic hydrometer according to claim 14, wherein the comparison means includes an amplifier which generates an output signal representative of the difference in voltage between the reference voltage and the voltage across the capacitor, and means to indicate the output of the amplifier.

17. An electronic hydrometer according to claim 16, wherein the amplifier is an integrated circuit operational amplifier.

18. An electronic hydrometer according to claim 16, wherein the probe is transformer-coupled to the rest of the circuitry.

19. An electronic hydrometer according to claim 18, wherein the A.C. resistance is a coupling transformer.

20. An electronic hydrometer according to claim 19, wherein the probe comprises two spaced apart electrodes having all but one of their ends embedded in a plastic material, the said one end of each electrode being exposed to the acid solution being monitored.

21. An electronic hydrometer according to claim 20, wherein the probe is secured to and carried by one of the normal battery cell caps of the battery whose acid solution is being monitored.

22. An electronic hydrometer according to claim 21, wherein the probe is transformer-coupled to the remainder of the circuitry.

23. An electronic hydrometer according to claim 22, wherein the A.C. resistance means is a coupling transformer coil.

* * * * *

UNITED STATES PATENT OFFICE
CERTIFICATE OF CORRECTION

PATENT NO. : 4,129,824
DATED : December 12, 1978
INVENTOR(S) : Edward P. Howes

It is certified that error appears in the above-identified patent and that said Letters Patent are hereby corrected as shown below:

Column 6, line 9, "is" should read --in--.

Column 6, line 17, "and" should read --an--.

Column 7, line 5, "is" should read --in--.

Column 9, line 40, "they" should read --the--.

Column 9, line 65, "on" should read --to--.

Column 10, line 14, "9" should read --6--.

Signed and Sealed this

Twenty-seventh Day of March 1979

[SEAL]

Attest:

RUTH C. MASON
Attesting Officer

DONALD W. BANNER
Commissioner of Patents and Trademarks